(12) United States Patent
Armstrong

(10) Patent No.: US 9,733,225 B2
(45) Date of Patent: Aug. 15, 2017

(54) SPECTROSCOPIC BREATH DETECTOR

(71) Applicant: Matthew David Armstrong, Kansas City, MO (US)

(72) Inventor: Matthew David Armstrong, Kansas City, MO (US)

(73) Assignee: Matthew David Armstrong, Kansas City, MO (US)

( * ) Notice: Subject to any disclaimer, the term of this patent is extended or adjusted under 35 U.S.C. 154(b) by 306 days.

(21) Appl. No.: 14/641,306

(22) Filed: Mar. 7, 2015

(65) Prior Publication Data

US 2016/0258917 A1 Sep. 8, 2016

(51) Int. Cl.
G01N 33/497 (2006.01)
G01N 33/00 (2006.01)
G01N 21/33 (2006.01)

(52) U.S. Cl.
CPC ..... *G01N 33/0047* (2013.01); *G01N 33/0011* (2013.01); *G01N 33/0016* (2013.01); *G01N 33/497* (2013.01); *G01N 21/33* (2013.01); *G01N 2033/4975* (2013.01)

(58) Field of Classification Search
CPC .................................................. G01N 33/497
See application file for complete search history.

(56) References Cited

U.S. PATENT DOCUMENTS

| | | | | |
|---|---|---|---|---|
| 2002/0081745 A1* | 6/2002 | Ross | ........................ | A61B 5/083 436/141 |
| 2003/0109794 A1* | 6/2003 | Phillips | .................. | A61B 5/097 600/543 |
| 2005/0051719 A1* | 3/2005 | Miller | .................. | G01N 27/622 250/287 |
| 2005/0065446 A1* | 3/2005 | Talton | .................... | A61B 5/097 600/529 |
| 2006/0073483 A1* | 4/2006 | White | .................. | C12Q 1/6825 435/6.1 |
| 2011/0259081 A1* | 10/2011 | Chou | .................... | G01N 29/022 73/23.42 |
| 2012/0302907 A1* | 11/2012 | Palmskog | .............. | A61B 5/082 600/532 |
| 2014/0127326 A1* | 5/2014 | Sood | .................... | G01N 33/497 424/649 |

(Continued)

*Primary Examiner* — Charlie Y Peng

(57) ABSTRACT

A replaceable spectroscopic detector used in volatile organic compounds testing devices, such as a portable breath testing device for roadside drug testing or a testing device for any air handling systems, such as those used for indoor agriculture, which reversibly sorb compounds and prepare a concentrated sample in a single gas cell configured for performing spectroscopy of the contents within the cell.

The disclosed invention comprising; one or more check valves, a source of electromagnetic radiation and an electromagnetic receiver that releasably connects to a volatile organic compounds testing device such that it is replaceable and is configured for performing spectroscopy and passing exhaled breath and/or airflow through a disposable and replaceable reversibly engaging cartridge comprising a reversible sorbent and a gas cell configured for spectroscopy. The invention further comprises a heater that preferably is included in the cartridge for heating the cell and desorbing the sorbed compounds preparing a concentrated sample inside the gas cell.

20 Claims, 2 Drawing Sheets

(56) References Cited

U.S. PATENT DOCUMENTS

2015/0305651 A1* 10/2015 Attariwala ............. A61B 5/097
 600/532
2016/0054294 A1* 2/2016 Rihani ................... G01N 21/27
 73/23.3
2016/0345910 A1* 12/2016 Ahmad .................. A61B 5/082

* cited by examiner

SPECTROSCOPIC BREATH DETECTOR

CROSS REFERENCE TO RELATED APPLICATION

Claiming priority date to Provisional Patent Application No. 61/949,214
Filing Date: Mar. 6, 2014
Name of Applicant: Matthew David Armstrong
Title of Invention: Smoky Breath Detector

STATEMENT OF FEDERALLY SPONSORED RESEARCH OR DEVELOPMENT

Not applicable

REFERENCE TO SEQUENCE LISTING

Not applicable

BACKGROUND OF THE INVENTION

For simplicity, this document primarily describes the invention as it relates to a breath volatile organic compounds testing device for roadside cannabis testing, but the invention is usable in other manners. One example is a volatile organic compounds testing device for any air handling system, especially those systems containing volatile organic compounds resulting from second hand smoke and/or indoor agricultural.

Current volatile organic compounds testing devices reversibly sorb and thermally desorb volatile organic compounds in exhaled breath and/or airflow to prepare a concentrated sample using a pre-concentrator or similar apparatus. The concentrated sample is transported into a separate gas cell where spectroscopy is performed. In such devices sequential desorption is commonly used to target selected compounds by purging the pre-concentrator of non-targeted compounds using heating and venting. These devices require a complex gas handling system, such as a vacuum pump or gas pump and switches.

It is advantageous to use a detector with replaceable parts to reduce contamination and a disposable pre-concentrator has been proposed. Yet, a replaceable spectroscopic detector that reversibly sorbs volatile organic compounds contained in exhaled breath and/or airflow and prepares a concentrated sample within a heated and disposable gas cell configured for spectroscopy has not been proposed.

BRIEF SUMMARY OF THE INVENTION

The purpose of the present invention is to provide a replaceable spectroscopic detector that releasably connects to a volatile organic compounds testing device for detecting and/or quantifying one or more volatile organic compounds in exhaled breath and/or airflow. For example, a breath volatile organic compounds testing device targeting compounds exhaled in breath a resulting from smoking any smokables and/or inhaling any vaporized substances, especially cannabis and other inhalants containing cannabinoids including tetrahydrocannabinol. The invention is further configured to reversibly engage a cartridge such that a gas cell configured for spectroscopy and reversible sorbent are disposable and replaceable. A method for using the invention is disclosed.

The invention is tubular in external appearance comprising a source of electromagnetic radiation and an electromagnetic receiver for performing spectroscopy of the contents within a reversibly engaging cartridge that is disposable and replaceable.

The cartridge forms a gas cell configured for spectroscopy and further comprises a reversible sorbent for reversibly sorbing volatile organic compounds exhaled in breath and/or airflow passing through the cartridge. The reversible sorbent is in fluid communication with the gas cell. The detector further comprises a heater for heating the gas cell and desorbing compounds from the reversible sorbent as a concentrated sample inside the same cell the compounds were sorbed.

The disposable and replaceable cartridge provides a means for fast sample turnaround. Directly following an analysis the hot and used cartridge is replaced with a fresh cartridge and another analysis may be performed. This eliminates the burn off time and cool down times required by systems using a non-replaceable pre-concentrator.

Currently proposed testing devices using a disposable reversible sorbent do so using a pre-concentrator and a separate spectroscopy cell. These are different from the disclosed invention because the disclosed invention does not transport a concentrated sample from one apparatus to another. That is volatile organic compounds are reversibly sorbed and a concentrated sample is prepared inside the gas cell configured for spectroscopy.

Performing spectroscopy of the concentrated sample inside the same cell it was formed in reduces concern of sample loss from transporting it from a pre-concentrator to a spectroscopy cell and provides a means to decrease the complexity of a gas handling system. To maintain sequential release of captured compounds, exhaled breath and/or airflow may be used to purge the cell.

Previously proposed devices reuse a spectroscopic cell and do not have the ability to or are difficult to clean and/or replace in the field. The disclosed invention addresses this difficulty by incorporating a disposable and replaceable reversibly engaging cartridge that forms a gas cell configured for spectroscopy. In addition, the invention heats the cell where sample may condense causing gunk build-up and sample loss in the cell if not heated. Furthermore, the invention releasably connects to a testing device in such a manner that the detector and cartridge are not reversibly engaging and are replaceable, or the detector releasably connects to a testing device and reversibly engages the cartridge such that a selection may be made to replace the cartridge or detector and cartridge with a fresh corresponding unit to address sample carryover, contamination and reduction of electrical spectroscopy component performance.

In areas that require high integrity sampling, such as law enforcement, the possibility of a contaminated device, especially the gas cell configured to perform spectroscopy and reversible sorbent component; for example cartridge, pre-concentrator, etc. are problematic. Therefore, a volatile organic compounds testing device with a spectroscopic detector that reversibly sorbs volatile organic compounds preparing a concentrated sample inside the same gas cell spectroscopy is performed and allows expired, used and/or hot parts to be replaced is desirable.

BRIEF DESCRIPTION OF SEVERAL VIEWS OF THE DRAWINGS

The drawings depict a proposed and preferred embodiment of one arrangement of parts to construct the invention, and are intended to be inclusive and additive, not restrictive.

DETAILED DESCRIPTION OF THE INVENTION

All components are constructed from materials capable of withstanding the operating temperature without denaturing or degrading.

Figure 3:
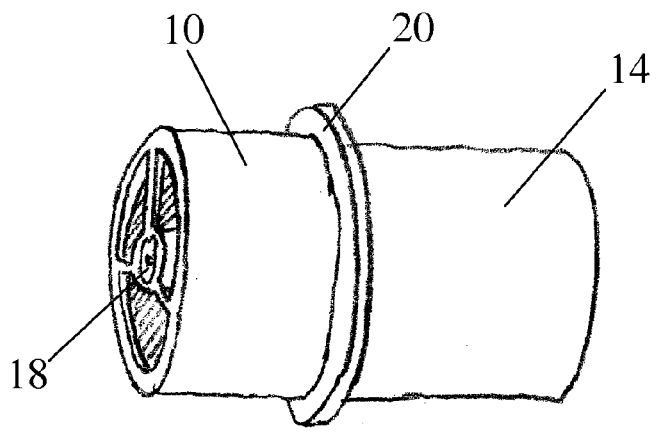
FIG. 3 is a perspective view of a spectroscopic breath detector with the detector and cartridge engaged according to the present invention

The preferred spectroscopic breath detector embodiment is tubular in external appearance, FIG. 3, and releasably connects to and brings in electrical communication a volatile organic compounds testing device such that exhaled breath and/or airflow is accepted and electrical parts are powered.

Figure 1:
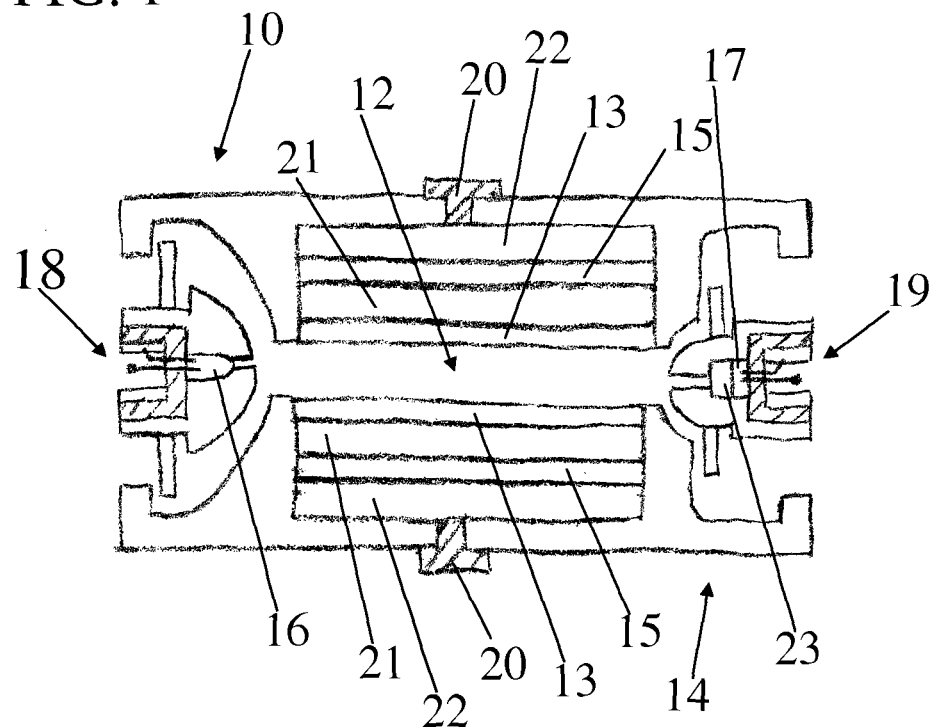
FIG. 1 illustrates a spectroscopic breath detector with the detector and cartridge engaged according to the present invention
Figure 2:
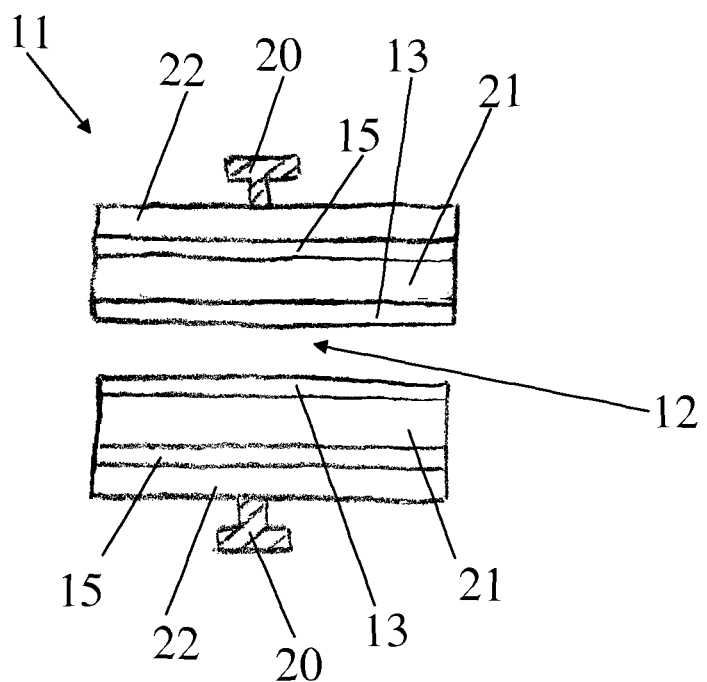
FIG. 2 illustrates a cartridge configured for use in a detector according to the present invention

The spectroscopic breath detector, FIG. 1, comprises an inlet check valve 10 for allowing exhaled breath and/or airflow to enter into a disposable and replaceable reversibly engaging cartridge 11, the cartridge 11 is observed as FIG. 2. The cartridge 11 comprises a gas cell 12 configured for performing spectroscopy of the contents within and a reversible sorbent 13 in fluid communication with the gas cell 12. The reversible sorbent 13 sorbs volatile organic compounds present in exhaled breath and/or airflow before the breath and/or airflow is expelled through the outlet check valve 14. A heater 15 heats the gas cell 12 and desorbs the sorbed compounds forming a concentrated sample inside the gas cell 12 where the check valves 10, 14 contain or reduce the loss of the sample by bracketing the cartridge 11. The gas cell 12 volume is preferably less than 5 cm$^3$.

Figure 4:
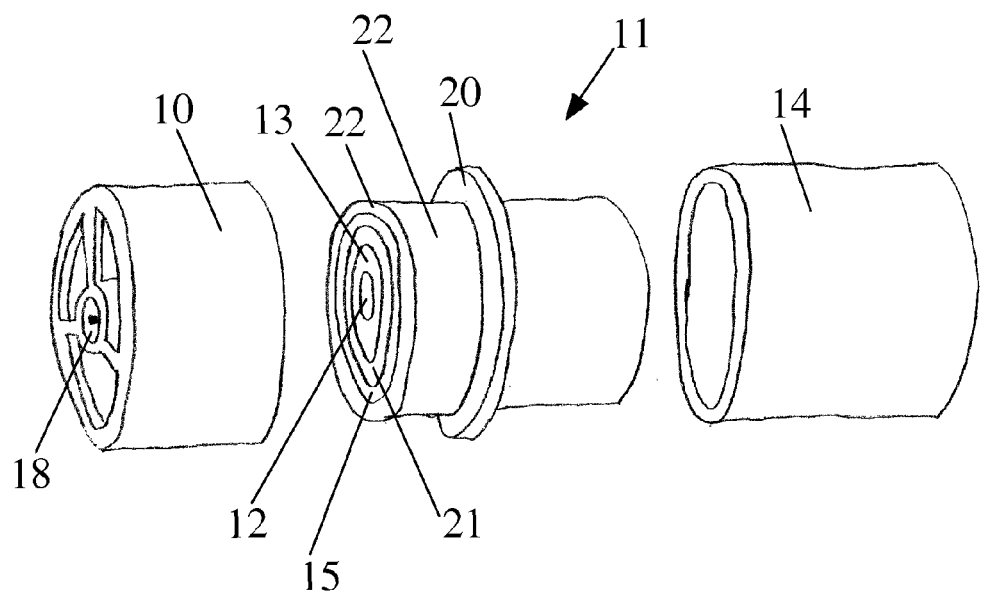
FIG. 4 is a perspective view of the spectroscopic breath detector with the detector and cartridge disengaged according to the present invention

The electrical spectroscopy components, source of electromagnetic radiation 16 and electromagnetic receiver 17 are configured for performing spectroscopy of the concentrated sample in the gas cell 12 by bracketing the cartridge 11. The source of electromagnetic energy 16 and the electromagnetic receiver 17 are wired to separate releasable electrical connectors 18, 19. Still in FIG. 1, the heater 15 is a thin film heater is part of the cartridge 11 and the check valves 10, 14 housing is extended for directing heat toward the gas cell 12. The check valves 10, 14 are electrically separated by a non-conductive material 20. The check valves 10, 14 are in-line check valves that also prevent the user from inhaling through the device. Check valve seals and springs not shown. The check valves 10, 14 reversibly engage the cartridge 11, FIG. 4, and releasably connect a testing device, perhaps using a squeezing mechanism, such that the detector as a whole, any part, parts, any combination of parts or any combinations of parts are replaceable.

Any parts can be combined. For example, as shown in FIG. 1, the inlet check valve 10 houses the source of electromagnetic radiation 16 and incorporates a connector 18 for releasably connecting a testing device.

FIG. 2 is a proposed disposable and replaceable cartridge 11 wherein the reversible sorbent 13 is any substance or group of materials that filter, capture, collect, retain, extract, sorb, etc. at least one volatile organic compound, when present, and allows at least one of the sorbed compounds to thermally desorb, release, vaporize, volatilize, evaporate, burn, combust, etc. into the surrounding gaseous phase and is used throughout this document to mean such, as well as related terminology such as sorb and desorb, etc. The reversible sorbent 13 is preferably a chemically-selective substance that releases compounds sequentially or simultaneously, including but not limited to stationary phases used in gas chromatography columns, more preferably a retention material containing a glycol, and most preferably a material containing polyethylene glycol or propylene glycol.

In the preferred embodiment, the reversible sorbent 13 is supported by a non-conductive substrate 21. The substrate 21 is preferably a low thermal expansion material, more preferably silica based, most preferably deactivated or fused silica.

In FIG. 1 and FIG. 2 the heater 15 is incorporated into the cartridge 11. The heater 15 is any material that generates heat when current flows through it, for example a metal or metal alloy wire or a thin plate or a source of electromagnetic radiation. The preferred heater 15 is a resistive metal, more preferably a thin film heater. The preferred embodiment comprises a thin film heater in contact with the substrate 21, but may be contained with or in the substrate 21. Lead lines, not shown, are preferably of the same material as the heater 15 are used to electrically engage the heater 15 from both ends to the check valve 10, 14 housings comprising an electrically conductive material in a reversible manner such that the heater 15 is capable of receiving powered. In FIG. 1, the check valves 10, 14 are constructed from an electrically conductive material, preferably a metal, more preferably aluminum.

The cartridge 11 includes a casing 22 forming a protective layer of non-conductive heat resistant material, preferably a polymer, more preferably polyimide, electrically separate the heater 15 from the check valve 10, 14 housings so they may act as releasable electrical connectors 18, 19 as is the matter in FIG. 1.

The cartridge 11 comprises a gas cell 12 where the energy travels from the source of electromagnetic radiation 16 into the cell 12 to interact with compounds desorbed from the reversible sorbent 13 before it encounters the electromagnetic receiver 17. In the preferred embodiment, FIG. 1 shows the source of electromagnetic radiation 16 and electromagnetic receiver 17 bracketing the cartridge 11 for performing spectroscopy.

The source of electromagnetic radiation 16 is any source that emits electromagnetic energy at any wavelengths, preferably a source providing a band or bands of light in the ultraviolet, visible and/or infrared regions, more preferably a light emitting diode or laser emitting diode. In FIG. 1, the source of electromagnetic radiation 16 is a light emitting diode.

The electromagnetic receiver 17 is any sensor that provides an output signal at a signal magnitude proportional to the intensity of electromagnetic energy received. The preferred electromagnetic receiver 17 is any photosensor including but are not limited to photoresistor, photomultiplier, phototransistor and photodiode, where the preferred sensor is a photodiode. In FIG. 1, the electromagnetic receiver 17 is a photodiode.

In this embodiment, FIG. 1, the source of electromagnetic radiation 16 and electromagnetic receiver 17 are wired to individual electrical connectors 18, 19 that releasably connect to a testing device, perhaps using a squeezing mechanism, allowing the spectroscopic electric components 16, 17 to be replaced. An optional optical band pass filter 23 for discriminating unwanted frequencies is place between the source of electromagnetic radiation 16 and electromagnetic receiver 17.

Where the target analyte is one or more cannabinoids, such as tetrahydrocannabinol, cannabidiol, and/or cannabinol the source of electromagnetic radiation 16 is a light emitting diode emitting light at about 280 nm and may be combined with a 280 nm polarized band pass filter 23. The electromagnetic receiver 17 is a photodiode, preferably an ultraviolet sensitive photodiode, more preferably an ultraviolet B only sensitive photodiode with a spectral range of 230-315 nm and a peak wavelength of 280 nm, one example of such a photodiode is a silicon carbide diode.

Operation

The invention may operate in any manner found suitable to sorb volatile organic compounds when exhaled breath and/or airflow passes through the invention, and thermally desorb compounds form a concentrated sample in a gas cell 12 configured for spectroscopy. Several manners for using the invention are proposed and not intended to be restrictive.

One manner of operation is now described. The invention reversibly engages to a volatile organic compounds testing device in a manner to accept exhaled breath and/or airflow and power electrical parts 15, 16, 17. Forced breath or airflow opens the check valves 10, 14 and the check valves 10, 14 close when the breath is not being forced or airflow is not being directed through the invention. Volatile organic compounds pass through the cartridge 11 where the reversible sorbent 13 sorbs volatile organic compounds before the breath and/or airflow exits the invention. Next, using heat the sorbed compounds are thermally desorbed into the gaseous phase of the gas cell 12. The closed check valves 10, 14 contain or reduce the loss of the generated concentrated sample in the gas cell 12.

Variations exist in the operation. One variation involves a means for reducing non-targeted compounds with low desorption temperatures. Before the invention accepts exhaled breath and/or airflow, the heater 15 is adjusted to a predetermined temperature above the ambient temperature and below the temperature the target compounds desorb, for example 50 degrees Celsius for cannabinoids. This allows some non-targeted compounds to pass through the cartridge 11 without being sorbed, while targeted compounds are reversibly sorbed.

Another variation involves another means for further removing non-targeted compounds from the gas cell 12 before performing spectroscopy and may be combined with the previous variation of operation. After exhaled breath and/or airflow has been accepted by the invention, heat is provided for desorbing non-targeted compounds with lower desorption temperatures than the target compounds and for retaining the targeted compounds, for example 100 degrees Celsius. The non-targeted compounds within the gaseous phase of the cell 12 may be expelled using exhaled breath and/or airflow. Finally, sufficient heat is provided to desorb the targeted compounds as a concentrated sample and spectroscopy may be performed.

Spectroscopic measurements may be performed of the gaseous phase contained in the gas cell 12 at any one time or a multitude of times anytime.

Lastly, the hot and used cartridge 11 or invention may be replaced with a fresh corresponding unit.

I claim:

1. A spectroscopic breath detector for a portable volatile organic compounds testing device, viewed externally as tubular in appearance, for performing spectroscopy of volatile compounds inside the spectroscopic breath detector, in which the spectroscopic breath detector comprises:

an electromagnetic receiver for providing an output signal at a signal magnitude proportional to the intensity of electromagnetic energy received,
an inlet check valve for allowing exhaled breath and/or airflow into
a replaceable cartridge comprising
    a gas cell configured for receiving exhaled breath and/or airflow and performing spectroscopy of volatile organic compounds inside said gas cell and
    a reversible sorbent for reversibly sorbing volatile organic compounds, when present, in fluid communication with said gas cell,
a heater for heating said cartridge and desorbing the sorbed compounds to form a concentrated sample of volatile organic compounds inside said gas cell,
an outlet check valve for allowing exhaled breath and/or airflow to exit said cell after encountering said cartridge,
a source of electromagnetic radiation for emitting electromagnetic energy, at any wavelengths, to interact with said concentrated sample of volatilized organic compounds that forms inside said gas cell,
a housing holding parts to form a spectroscopic device wherein said source of electromagnetic radiation and said electromagnetic receiver bracket said gas cell according to the flow through said gas cell,
a spectroscopic detector for performing spectroscopy on volatile organic compounds inside said housing,
a releasable electrical connector or more for said source of electromagnetic radiation, heater and electromagnetic receiver,
wherein said inlet check valve and/or said outlet check valve is an in-line check valve,
said inlet check valve and said outlet check valve bracket said gas cell according to the flow through said cartridge,
    said spectroscopic breath detector configured
        for reversibly sorbing volatile organic compounds from exhaled breath and/or airflow inside said housing,
        forming the concentrated sample of volatile organic compounds inside said housing and
        performing spectroscopy on the concentrated sample of volatile organic compounds inside said housing
        for not transferring the volatile organic compounds to a separate device such that sample collection, forming the concentrated sample and spectroscopy of volatile organic compounds are performed inside said housing,
said spectroscopic breath detector is configured for reversibly engaging said cartridge or any part, parts, combination of parts, or combinations of parts that include said cartridge and
further configured for releasably connecting to and bringing in communication a portable volatile organic compounds testing device such that exhaled breath and/or airflow is accepted and electrical parts are powered.

2. A spectroscopic breath detector according to claim 1 wherein said cartridge comprises any combination of parts that comprises said spectroscopic breath detector, especially the combination of said gas cell, said reversible sorbent, said heater and said electrical connector.

3. A spectroscopic breath detector according to claim 1 wherein one said valve houses said electromagnetic receiver or said source of electromagnetic radiation, or one said valve houses said electromagnetic receiver and a second said valve houses said source of electromagnetic radiation.

4. A spectroscopic breath detector according to claim 1 wherein said heater is a thin film heater.

5. A spectroscopic breath detector according to claim 1 wherein one of said check valves houses said source of electromagnetic radiation or electromagnetic receiver and at least one said electrical connector, or one said valve houses said source of electromagnetic radiation and second said valve houses said electromagnetic receiver and one or more of said valves houses at least one electrical connector.

6. A spectroscopic breath detector according to claim 1 wherein said cartridge further comprises one or more said valve, wherein at least one said valve houses one or more parts from a selection of said electromagnetic radiation, said electromagnetic receiver and said electrical connector.

7. A spectroscopic breath detector according to claim 1 wherein said inlet check valve and said outlet check valve bracket said gas cell is changed to said inlet check valve and said outlet check valve do not bracket said gas cell.

8. A spectroscopic breath detector according to claim 1 wherein said source of electromagnetic radiation is a light emitting diode.

9. A spectroscopic breath detector according to claim 1 wherein said electromagnetic receiver is a photodiode.

10. A spectroscopic breath detector according to claim 1 wherein said cartridge comprises said reversible sorbent and said reversible sorbent is a chemically-selective substance, said chemically-selective substance is preferably a glycol, more preferably said chemically-selective substance is selected from propylene glycol or polyethylene glycol.

11. A housing holding parts to form a spectroscopic device wherein said source of electromagnetic radiation and said electromagnetic receiver bracket said gas cell according to the flow through said gas cell according to claim 1 is changed to a housing holding parts to form a spectroscopic device wherein said source of electromagnetic radiation and said electromagnetic receiver are in-line with the flow through said gas cell.

12. A housing holding parts to form a spectroscopic device wherein said source of electromagnetic radiation and said electromagnetic receiver bracket said gas cell according to the flow through said gas cell according to claim 1 is changed to a housing holding parts to form a spectroscopic device.

13. A spectroscopic breath detector according to claim 10 wherein said cartridge further comprises said chemically-selective substance supported by a substrate.

14. A spectroscopic breath detector according to claim 13 wherein said cartridge further comprises a casing, said casing is preferably non-conductive, more preferably said casing comprises polyimide.

15. A spectroscopic breath detector is configured for reversibly engaging said cartridge or any part, parts, combination of parts, or combinations of parts that include said cartridge according to claim 1 is changed to said spectroscopic breath detector is replaceable and not configured for reversibly engaging said cartridge or any part, parts, combination of parts, or combinations of parts.

16. A spectroscopic breath detector according to claim 1 wherein said cartridge comprises:
  any combination of parts that make up said spectroscopic breath detector and
  said reversible sorbent being a chemically-selective substance, said chemically-selective substance is preferably a glycol, more preferably said chemically-selective substance is selected from propylene glycol or polyethylene glycol
  a casing, wherein said casing is preferably non-conductive, more preferably polyimide.

17. A spectroscopic breath detector according to claim 1 wherein said spectroscopic breath detector is further configured for:
  one said valve housing said source of electromagnetic radiation,
  a second said valve housing said electromagnetic receiver, and
  at least on said valve comprises one or more said electrical connector,
  said cartridge comprising;
    said reversible sorbent which is a chemically-selective substance,
    said heater in close proximity to said chemically-selective substance and
    a casing of which is preferably not electrically conductive, more preferably said casing comprises polyimide.

18. A spectroscopic breath detector according to claim 17 wherein
  said heater is a thin film heater,
  said source of electromagnetic radiation is a light emitting diode,
  said electromagnetic receiver is a photodiode and
  said chemically-selective substance comprises a glycol.

19. A spectroscopic breath detector according to claim 1 wherein said source of electromagnetic radiation for emitting electromagnetic energy, at any wavelengths, emits energy in the ultraviolet and/or visible range, preferably in the range of 10 nm to 750 nm, more preferably in the range of 200 nm to 550 nm.

20. A spectroscopic breath detector for a portable volatile organic compounds testing device for performing spectroscopy of volatile compounds inside the spectroscopic breath detector, in which the-spectroscopic breath detector comprises:
  an electromagnetic receiver for providing an output signal at a signal magnitude proportional to the intensity of electromagnetic energy received,
  an inlet for allowing exhaled breath and/or airflow into
  a replaceable cartridge comprising
    a gas cell configured for receiving exhaled breath and/or airflow and performing spectroscopy of volatile organic compounds inside said gas cell and
    a reversible sorbent for reversibly sorbing volatile organic compounds, when present, in fluid communication with said gas cell, and
  said cartridge comprises any combination of parts that comprises said spectroscopic breath detector
  a heater for desorbing the sorbed compounds to form a concentrated sample of volatile organic compounds inside said gas cell,
  an outlet for allowing exhaled breath and/or airflow to exit said cell after encountering said cartridge,
  a source of electromagnetic radiation for emitting electromagnetic energy, at any wavelengths, to interact with said concentrated sample of volatilized organic compounds that forms inside said gas cell,
  a housing holding parts to form a spectroscopic device,
  a spectroscopic detector for performing spectroscopy on volatile organic compounds inside said housing,
  a releasable electrical connector or more for said source of electromagnetic radiation, heater and electromagnetic receiver,
  said spectroscopic breath detector configured
    for reversibly sorbing volatile organic compounds from exhaled breath and/or airflow inside said housing, forming the concentrated sample of volatile organic compounds inside said housing and performing spectroscopy on the concentrated sample of volatile organic compounds inside said housing for not transferring the volatile organic compounds to a separate device such that sample collection, forming the concentrated sample and spectroscopy of volatile organic compounds are performed inside said housing, said spectroscopic breath detector is configured for reversibly engaging said cartridge or any part, parts, combination of parts, or combinations of parts that include said cartridge and further configured for releasably connecting to and bringing in communication a portable volatile organic compounds testing device such that exhaled breath and/or airflow is accepted and electrical parts are powered.

* * * * *